(12) United States Patent
Kantzas et al.

(10) Patent No.: US 10,281,535 B2
(45) Date of Patent: May 7, 2019

(54) SYSTEMS AND METHODS FOR SAMPLING FLUIDS USING NUCLEAR MAGNETIC RESONANCE (NMR)

(71) Applicant: PERM Instruments Inc., Calgary (CA)

(72) Inventors: Apostolos Kantzas, Calgary (CA); Serguei I. Krioutchkov, Calgary (CA); Zheng Yin Wang, Calgary (CA)

(73) Assignee: PERM INSTRUMENTS INC., Calgary (CA)

(*) Notice: Subject to any disclaimer, the term of this patent is extended or adjusted under 35 U.S.C. 154(b) by 274 days.

(21) Appl. No.: 15/252,979

(22) Filed: Aug. 31, 2016

(65) Prior Publication Data

US 2017/0074952 A1 Mar. 16, 2017

Related U.S. Application Data

(60) Provisional application No. 62/216,092, filed on Sep. 9, 2015.

(51) Int. Cl.
| | | |
|---|---|---|
| *G01R 33/30* | (2006.01) | |
| *G01R 33/00* | (2006.01) | |
| *G01N 24/08* | (2006.01) | |
| *G01R 33/34* | (2006.01) | |
| *G01R 33/383* | (2006.01) | |

(52) U.S. Cl.
CPC ....... *G01R 33/307* (2013.01); *G01R 33/0052* (2013.01); *G01N 24/081* (2013.01); *G01R 33/305* (2013.01); *G01R 33/34053* (2013.01); *G01R 33/383* (2013.01)

(58) Field of Classification Search
None
See application file for complete search history.

(56) References Cited

U.S. PATENT DOCUMENTS

| | | | |
|---|---|---|---|
| 6,346,813 | B1 | 2/2002 | Kleinberg |
| 6,825,657 | B2 | 11/2004 | Kleinberg et al. |
| 7,463,027 | B2 | 12/2008 | Prammer et al. |
| 8,659,293 | B2 * | 2/2014 | Krioutchkov ........ G01N 24/081 324/307 |
| 2009/0072825 | A1 | 3/2009 | Prammer et al. |
| 2009/0128144 | A1 | 5/2009 | Freedman et al. |
| 2010/0001730 | A1 | 1/2010 | Stephenson et al. |

OTHER PUBLICATIONS

J.D. Jackson. Classical Electrodynamics, 3rd edition, 1998, Wiley (page from chap. 2).

* cited by examiner

*Primary Examiner* — Paresh H Patel
(74) *Attorney, Agent, or Firm* — Morgan, Lewis & Bockius LLP (57) ABSTRACT

Systems and methods for sampling fluids using nuclear magnetic resonance (NMR). Specifically the system is related to a robust field oriented piping system having an improved pipe design for use at oil and gas well heads. The piping system includes integral coils for transmitting an NMR pulse sequence and detecting NMR signals and can be used as a component of an NMR instrument. The systems and methods described herein enable obtaining and analyzing NMR spectra of multi-phase in stationary and flowing states.

21 Claims, 5 Drawing Sheets

SYSTEMS AND METHODS FOR SAMPLING FLUIDS USING NUCLEAR MAGNETIC RESONANCE (NMR)

FIELD OF THE INVENTION

This application is related to systems and methods for sampling fluids using nuclear magnetic resonance (NMR). Specifically the system is related to a robust field oriented piping system having an improved pipe design for use at oil and gas well heads. The piping system includes integral coils for transmitting an NMR pulse sequence and detecting NMR signals and can be used as a component of an NMR instrument. The systems and methods described herein enable obtaining and analyzing NMR spectra of multi-phase in stationary and flowing states.

BACKGROUND OF THE INVENTION

As described in Applicant's issued U.S. Pat. No. 8,659,293 issued Feb. 25, 2014 and incorporated herein by reference, in the oil and gas industry, it is desirable for producers of heavy crude oil and bitumen, and in particular during cyclic steam stimulation (CSS), steam assisted gravity drainage (SAGD) and thermal assisted gravity drainage (TAGD) operations, to obtain accurate measurements of the percentage of water contained in a produced emulsion flow of oil, water and gas.

Generally, it is desired to have this measurement taken on a regular basis from the piping infrastructure near the production wells where the fluid stream is under considerable pressure and temperature. As is known, typical pressures in a SAGD operation can be in the range of 100 to 600 psi (690 kPa to 4140 kPa) or greater and temperatures can be upwards of 400° F. (204° C.) and higher. As a result, piping and control systems engineered for these environments are robust which can make the continuous monitoring of the contents within the piping relatively difficult due to the temperatures and pressures within the piping that can prevent the use of various types of sensing/monitoring equipment.

It is known, that nuclear magnetic resonance (NMR) technology can accurately and quickly measure the relative amounts of oil, water and gas in an encapsulated sample of fluid. It is also known that in order to enable NMR systems to operate within such an environment, the container holding a sample of fluid must be made of nonmagnetic material. The nonmagnetic material may be a non-metallic material.

In general, conventional pipes used to convey hydrocarbon fluids from wells have a magnetic component to them. As magnetic pipes create problems for nuclear magnetic resonance (NMR) measurement systems, the use of NMR requires specialized piping systems that enable NMR systems to operate. That is, as is known, NMR systems function by applying an external static magnetic and a pulsating electromagnetic field to a sample to determine the components of the sample in terms of water, oil and gas content. Various NMR systems are described in US Patent Publication No. 2009/0128144; US Patent Publication No. 2009/0072825; U.S. Pat. No. 6,346,813; U.S. Pat. No. 7,463,027; US Patent Publication No. 2010/0001730; and U.S. Pat. No. 6,825,657.

As NMR systems use magnetic fields, any magnetic materials located inside or near the magnetic field will damage the homogeneity of the magnetic field and undermine the accuracy and sensitivity of the NMR system. As such, there is generally a need for systems that mitigate these problems, and more specifically there has been a need for improved pipe designs that can be used with an NMR metering tool or system to increase the accuracy and sensitivity of an NMR meter in the field.

SUMMARY OF THE INVENTION

In accordance with the invention, there is provided a pipe system for enabling nuclear magnetic resonance (NMR) analysis of gases and liquids within the pipe system comprising: at least one inner non-magnetic layer having an inner diameter $D1$ defining an inner fluid passage and an outer diameter $D3$, the at least one inner non-magnetic layer operatively supporting an NMR coil having an outer diameter $D2$; and an outer non-magnetic layer and where the at least one inner non-magnetic layer is operatively supported within the outer non-magnetic layer to define an outer fluid passage between the at least one inner non-magnetic layer and the outer non-magnetic layer, the outer fluid passage having an outer diameter $D4$.

In another embodiment $D4/D2=\sqrt{2}$ with a matching accuracy better than 2%.

In further embodiments, the outer non-magnetic layer is titanium alloy, hastelloy alloy or inconel alloy.

In another embodiment, the pipe system comprises an outer shield layer that is operatively connected to the inside of the outer non-magnetic layer and is configured to constrain the magnetic field generated by the coil within the inner shield layer.

In yet another embodiment, the outer shield layer comprises a non-magnetic layer such as copper or a material having a higher conductivity than copper.

In one embodiment, the outer shield layer length is at least four times $D2$.

In another embodiment, the coil is copper or a material having a higher conductivity than copper.

In one embodiment, the at least one inner non-magnetic layer is two thermoplastic layers and the coil is supported by a first inner thermoplastic layer and a second thermoplastic layer surrounds the first inner thermoplastic layer.

In another embodiment, the inner non-magnetic layer comprises one or more of: a thermoplastic, polyetheretherketone (PEEK), Teflon and TORLON.

In yet another embodiment, the outer layer material is a non-magnetic metallic material, or a nonmetallic material.

In a further embodiment, the outer layer material comprises one or more of: titanium, titanium alloy, hastelloy alloy, inconel alloy, beryllium copper alloy, and fiberglass reinforced plastic.

In one embodiment, the Q-factor, or quality factor, of the resonant circuitry is between 5 and 10. In another embodiment, the Q-factor is above 20.

In yet another embodiment, the coil length is at least two times of $D2$.

In another embodiment, the pipe system includes at least one coil supporting member, the at least one coil supporting member being configured to support the coil in position with respect to the outer layer and to allow fluid flow within the inner and outer fluid passages.

In one embodiment, the inner layer comprises: a coil layer configured to provide structural support for the coil; and a protection layer configured to protect the outer surfaces of the coil.

In one embodiment, the coil layer comprises one or more notches configured to receive the coil.

In another aspect the invention provides a method of manufacturing a pipe system for enabling nuclear magnetic resonance (NMR) analysis of gas and liquids within the pipe system, the method including the steps of: providing at least one inner non-magnetic layer having an inner diameter D1 defining an inner fluid passage and an outer diameter D3, the at least one inner non-magnetic layer operatively supporting an NMR coil having an outer diameter D2; and providing an outer non-magnetic layer and where the at least one inner non-magnetic layer is operatively supported within the outer non-magnetic layer to define an outer fluid passage having an diameter D4 between the at least one inner non-magnetic layer and the outer non-magnetic layer.

In one embodiment, the copper coil is produced by winding copper wire around a coil layer, the coil layer forming at least part of the inner non-magnetic layer.

In another embodiment, the method includes the steps of: machining the coil such that the coil is configured to hold the shape after it is machined; and encasing the coil in an epoxy resin, the epoxy resin forming at least part of the inner non-magnetic layer.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

DETAILED DESCRIPTION OF THE INVENTION

With reference to the figures, a pipe system 10 used for NMR measurement of the composition of fluids flowing within the pipe are described. The pipe system is particularly applicable for conducting NMR measurements in a high pressure, high temperature environment.

Rationale

The subject invention seeks to overcome a number of problems in determining the relative quantities of different materials flowing within a pipe using NMR technology to in order to improve the accuracy and efficiency by which such measurements are made. More specifically, the subject invention:

Enables the NMR signal to be collected from both inside and outside the coil which improves the signal to noise ratio (SNR) of the NMR system. In certain embodiments, the signal to noise ratio may be doubled due to doubled sample volume.

Increases the processing capacity of an NMR instrument or system configured to a pipe system by increasing the cross-sectional flow area for the fluids within the pipe system. In some cases, the processing capacity may be doubled.

Reduces plastic layers between the coil and outer containment sleeves whilst maintaining required structural strength.

Improves the filling factor, which is the ratio of sample volume to coil volume. Certain embodiments may allow the filling factor to be greater than one. Certain embodiments may allow the filling factor to be doubled.

Decreases the coil diameter $$\left(\text{e.g. by a factor of } \frac{1}{\sqrt{2}}\right),$$

which improves the NMR instrument acquisition time. Smaller coil diameter means shorter acquisition time. Shorter acquisition time is a key parameter for measuring fast relaxation components like heavy bitumen samples.

Scope of Language

All terms used within this specification have definitions that are reasonably inferable from the drawings and description. In addition, the language used herein is to be interpreted to give as broad a meaning as is reasonable having consideration to the rationale of the subject invention as understood by one skilled in the art. It is also to be understood that prior art cited during prosecution of the subject patent application may not have been specifically identified prior to the drafting of the subject document and that various amendments may be introduced during prosecution that require amendment of terms to provide clarity to the distinctions between the subject invention and that prior art and that such amendments are reasonably inferable having consideration to the document as a whole and the rationale of the invention.

Introduction

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

Figure 1:
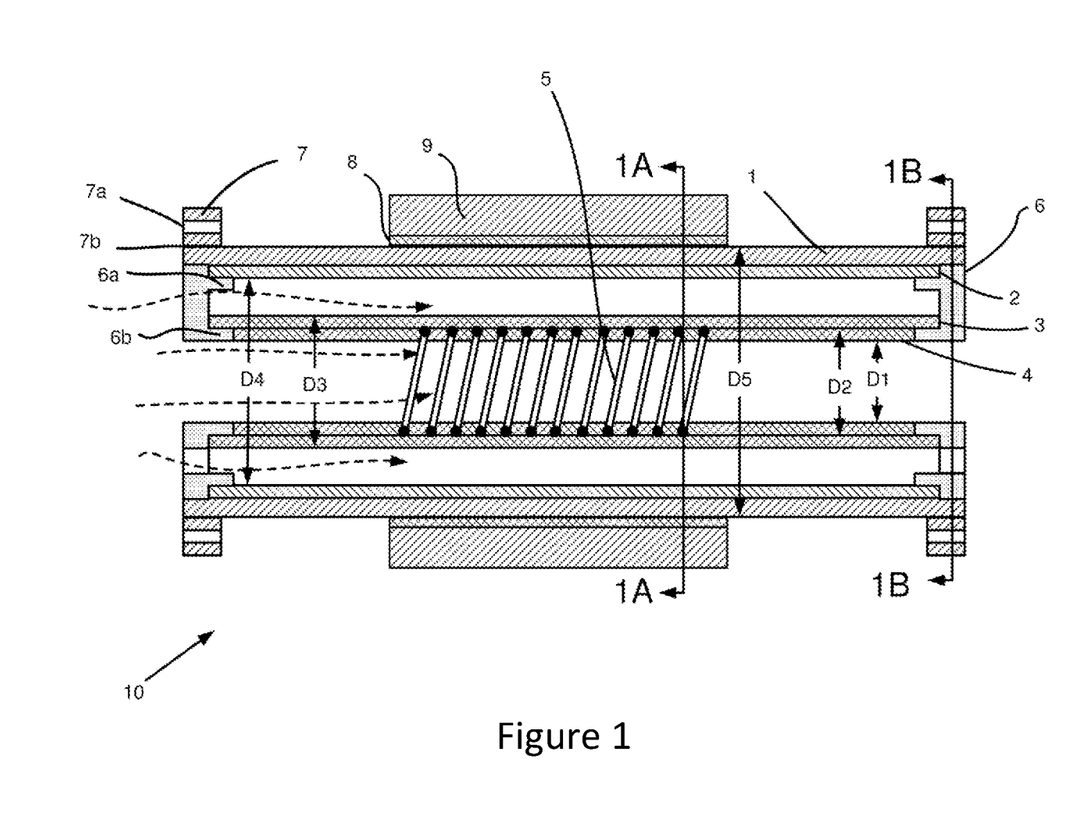
FIG. 1 is a schematic cross-sectional diagram of the general design concepts of a pressure pipe used for NMR measurement of the composition of fluids flowing within the pipe in accordance with one embodiment of the invention.
Figure 1A:
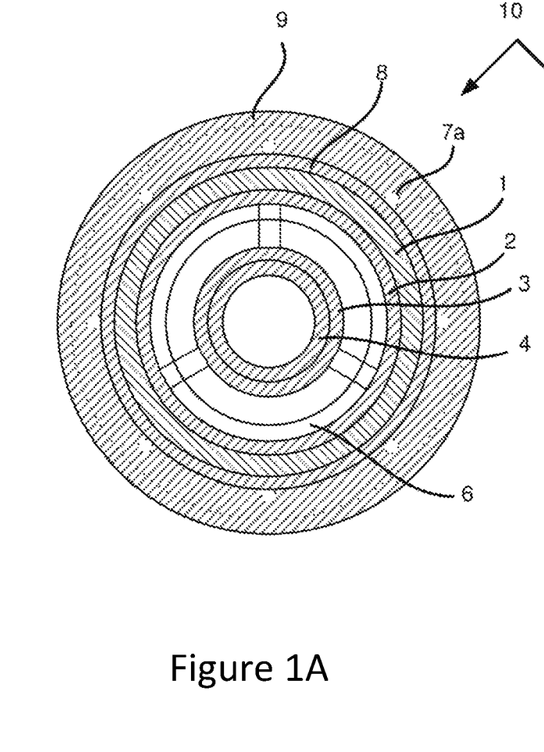
FIG. 1A is a schematic cross-sectional diagram of the general design concepts of a pressure pipe used for NMR measurement of the composition of fluids flowing within the pipe in accordance with one embodiment of the invention at line 1A-1A of FIG. 1.
Figure 1B:
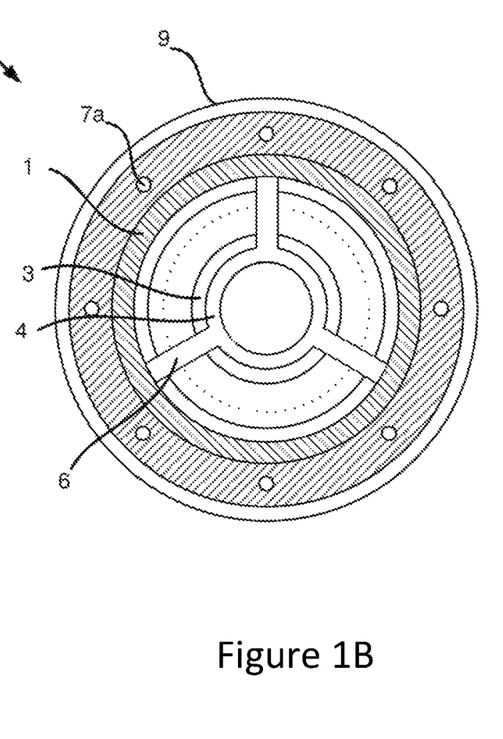
FIG. 1B is a schematic cross-sectional diagram of the general design concepts of a pressure pipe used for NMR measurement of the composition of fluids flowing within the pipe in accordance with one embodiment of the invention at line 1B-1B of FIG. 1.

As shown in FIGS. 1, 1A and 1B, the general design of a pipe system 10 enabling NMR measurements to be conducted within the pipe system are described. The pipe system when configured to NMR equipment is used to determine the composition of fluids flowing within the pipe and, in particular, in a high temperature and high pressure environment. FIG. 1 shows a cross-section of a pipe system along the length of the pipe system. FIG. 1A shows a cross section through a middle section of the pipe system and 1B shows a cross section of the pipe through a coil support disk.

As shown, the pipe system includes a plurality of layers and structures including:
 a. Outer non-magnetic metal layer 1 (Layer 1).
 b. Outer shield layer 2 (Layer 2).
 c. Inner non-magnetic layer comprising:
   1. Protective layer 3(Layer 3).
   2. Coil layer 4 (Layer 4).
 d. Coil 5.
 e. Coil supports (e.g. in the form of a supporting disk 6 for each end).
 f. Pipe flange 7 for each end.
 g. Magnet lining layer (Layer 8).
 h. Permanent Magnet (Layer 9).

As shown in FIG. 1, each of the layers has inner and outer diameters. For the purposes of description, D1 is the inner diameter that defines an inner fluid passage, D2 is the outer diameter of the coil, D3 is the outer diameter of the protective layer 3, D4 is the inner diameter of one or both of layers 1 and 2, and D5 is the outer diameter of layer 1 and inner diameter of magnet lining layer 8.

Generally, the outer layer material is non-magnetic with mechanical characteristics enabling its use as a high temperature and high pressure vessel. The pipe system 10 includes appropriate connectors (such as a standard pipe flange 7 having bolt holes 7a and threaded connector 7b) integrated to the pipe system enabling its connection to other piping systems (not shown).

The thickness of the outer layer 1 is primarily determined by the temperature and pressure performance requirements to safely contain the fluid. Typically, in an application such as the measurement of the composition of fluids returned from a SAGD operation, the pressure and temperature performance requirements of the outer layer are 100 to 600 psi (690 kPa to 4140 kPa) or greater and temperatures upwards of 400° F. (204° C.).

Using titanium or titanium alloys may enable a decreased thickness compared with other materials such as stainless steel. The lower thickness of the outer layer enables a larger sample space (D4) and coil size (D2) for a given pipe diameter. The lower thickness also means smaller outside diameter (D5) for a given pipe size, outside diameter (D5) determines the diameter of the permanent magnet. The permanent magnet is preferably a Halbach magnet as such magnet systems allow a smaller magnet size that will also will decrease the magnet weight and the expensive material used to build it.

The outer layer 1 can be any non magnetic metallic or nonmetallic material, which is strong enough for given temperature and pressure conditions. Commonly used non-magnetic materials for this application include titanium alloy, hastelloy alloy, inconel alloy, beryllium copper alloy or even fiberglass reinforced plastic.

The inner non-magnetic inner layer 2 may comprise the same non-magnetic material as the coil 5 or a material having a higher electrical conductivity than the coil material. The coil material is typically copper as described below. The purpose of layer 2 is to provide magnetic-noise shielding from outside the pipe and maximizing the Q factor of the coil.

Q-factor, or quality factor, of the resonant circuitry that includes the coil 5 and serves as a sensor of the NMR signal is defined by the standard relation:

$$Q = 2\pi \frac{\text{Energy stored}}{\text{Energy dissipated per cycle}}$$

Depending on the conditions of operations it can be advantageous to have a lower value of the Q-factor. In this case the system can be used without layer 2.

Lower Q-factor (5 to 10) is needed in order to reduce or minimize the acquisition time of the instrument, which is very important for measuring heavy bitumen fast relaxation components.

Higher Q-factor (above 20) may be particularly advantageous when the filling factor is below 0.1 or when the water and oil percentage in the sample is less than 10% in order to get a reasonable high SNR (e.g. a signal to noise ratio of above 50). In other embodiments, if there is enough water or oil in the samples, the Q-factor may be lower (e.g. below 20 but above 5) in order to simplify the design (for example by omitting layer 2).

In a preferred embodiment, shield layer 2 is a copper design inside outer layer 1. Generally, the shield layer 2 will improve the Q factor of the coil when the gap between shielding layer (layer 2) and the coil is limited. However, as noted above, layer 2 is not necessarily required.

Coil Design and Dimensions

Figure 2:
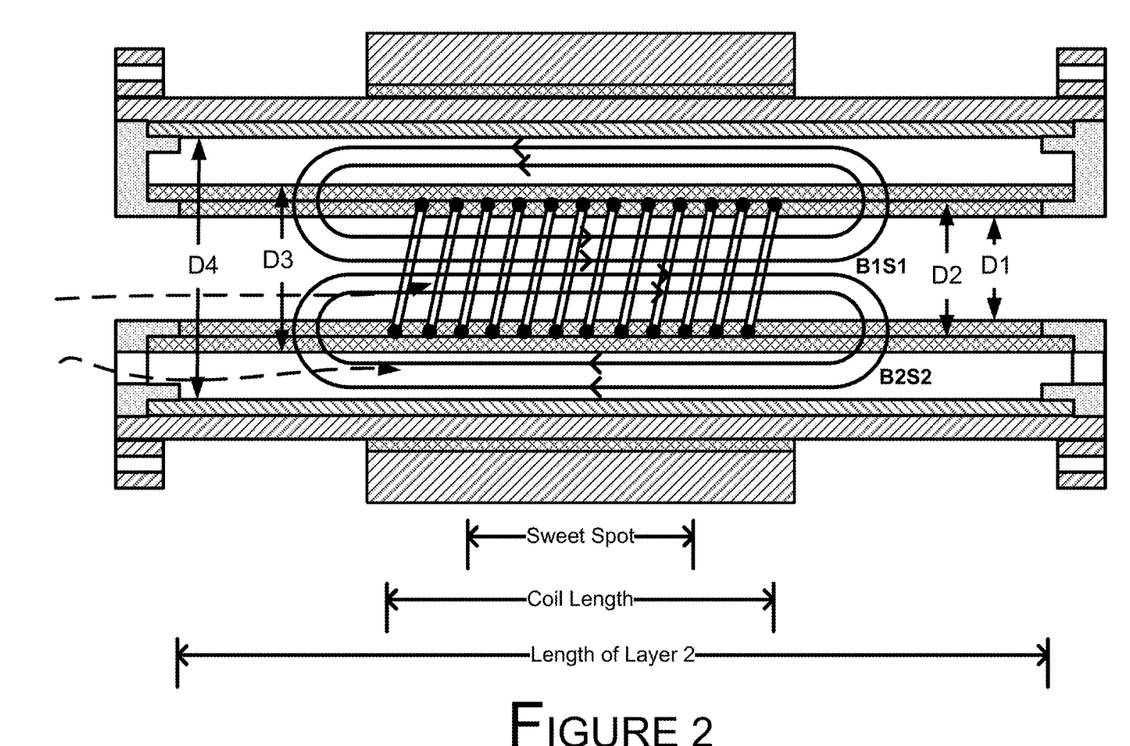
FIG. 2 is a schematic cross-sectional diagram illustrating the relative dimensions and various of components of an embodiment of the pipe system.

In order to make the measuring area (sweet spot) long enough the coil length (as shown in FIG. 2) should be at least two times of D2 and the Layer 2 length should be at least four times of D2, which will make the sweet spot area at least as long as D2.

The diameter of the coil D2 may be $\sqrt{2}$ times smaller than the inner diameter D4 of the non magnetic pipe (including layer 2, if incorporated into the design). In other words D4/D2=$\sqrt{2}$. (Exact match D4/D2=$\sqrt{2}$ is the optimal ratio, and the matching error should be better than 2%). That is, the ratio D4/D2 may be between about 1.38 and 1.44. It will be appreciated that other embodiments may have other ratios of D4:D2.

According to Gauss's law for magnetism the net magnetic flux out of a closed surface is zero, which means B1S1+B2S2=0. The coil will generate a radio frequency (RF) magnetic field around the coil, inside and outside of the coil. That is, the magnetic flux will flow one direction inside the coil and return in substantially the opposite direction outside the coil. Therefore, for a coil, this means that the total magnetic flux flowing inside the coil is equal to the total magnetic flux flowing outside the coil. B1 denotes the RF magnetic field strength inside the coil and B2 denotes the field strength outside of the coil. S1 is the cross area inside the coil and S2 is the cross area outside of the coil. In the case where the magnetic flux outside the coil is constrained (e.g. by being shielded) it may be assumed that area S2 corresponds to the area inside the magnetic shielding and outside the coil. Due to the restriction of D4/D2=$\sqrt{2}$, the area inside the coil, S1, is the same as the area, S2, between the coil and the shielding metal layer 2. Therefore, in this case, S1=S2 and B1=−B2 (the negative sign indicating that the magnetic flux direction is different).

Under this condition the magnitude of the RF magnetic field inside the coil and outside the coil will be almost the same. That is, in the middle part of the coil (sweet spot measuring area), the magnetic field both inside and outside of the coil is uniform. This "sweet spot" condition stems from the fact that the high frequency EM field will induce currents in the copper layer. Those currents will reach a level such that no magnetic field will get outside of the pipe. By constraining the magnetic flux within the pipe, the magnetic flux may be substantially uniform across the cross sectional area of the pipe. This means that the fluid passing through the pipe will experience substantially the same magnetic field strength regardless of whether it is near the centre or near the outside of the pipe.

The characteristic depth of penetration of the EM field into copper at 1 MHz frequency is about 66 micrometers. With 5 times this value (0.33 mm) only a small portion of 1 percent of magnetic field will escape the metal-confined area. As a result, this determines the minimum thickness of the copper layer (layer 2) for the system to work efficiently. In practice, the thickness of the copper layer should be more than that stated above (i.e. 0.33 mm) in order to provide durability of the material working in contact with oil-water flow. This argument applies to any and all design pipe diameters.

If the copper layer is not used, then the thickness of the high-pressure pipe itself must be sufficient to achieve the same results having consideration to the lower conductivity of the outer pipe metal (layer 1) compared to the copper conductivity.

Accordingly, with the condition of magnetic flux conservation within the system and with Maxwell equation $$\nabla \cdot B = 0 \qquad \text{[Reference 1]}$$

indicates that the magnetic flux inside the coil and outside the coil will be the same.

Furthermore, in another Maxwell equation $$\nabla \times B = \mu_0 \left( J + \varepsilon_0 \frac{\partial E}{\partial t} \right) \qquad \text{[Reference 1]}$$

the second term on the right $$\left( \varepsilon_0 \frac{\partial E}{\partial t} \right)$$

is neglible. Moreover, the system dimensions are much smaller than the wavelength of EM radiation at frequencies used, normally low field NMR frequency is around several MHz. The wavelength of EM radiation in the MHz range is typically in the order of 10 s to 100 s of meters which is generally larger than, for example, the diameter of the pipe. Accordingly, using a standard procedure with the equation $$\nabla \times B = \mu_0 J$$

and assuming uniform distribution of the coil turns, the above shows the RF magnetic field is uniform inside the coil, outside the coil and their values are the same (see [reference 1], for example. Accordingly, the magnetic field outside the coil will only be equal to that inside the coil when the magnetic field is constrained by a magnetic shield such that the area inside and the area outside the coil is the same. That is, without the shielding layer the magnetic field lines will be further apart outside the coil than inside the coil.

Layers 3 and 4 serve the purpose of protecting the coil from the flowing fluids and to provide structural rigidity for coil and its placement within the flow. Layers 3 and 4 materials are non-conductive materials having a high hardness enabling long-term performance in a high temperature oil-water mixture flow.

Figure 3:
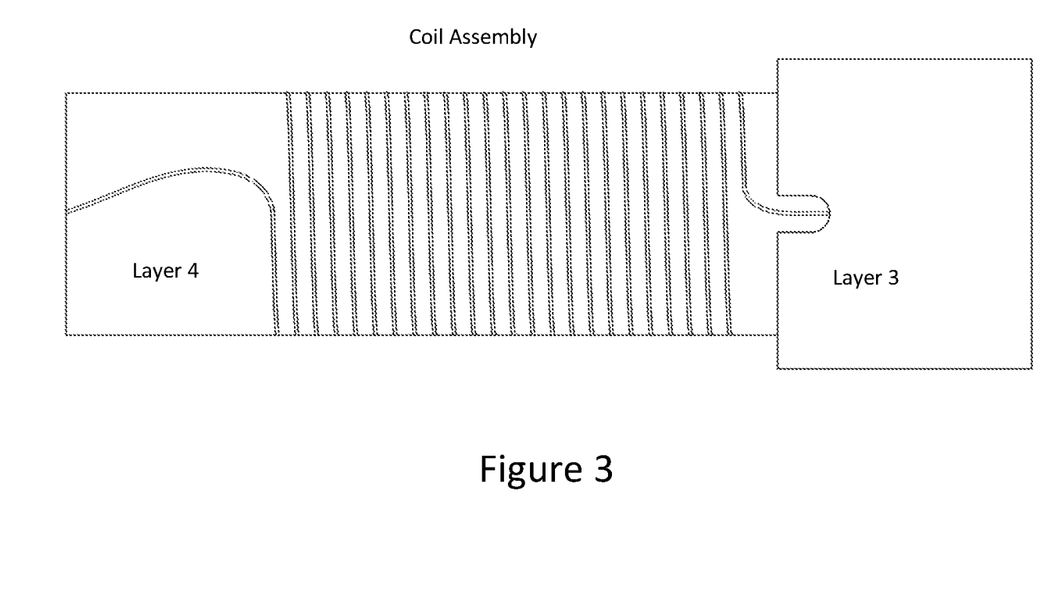
FIG. 3 is a diagram illustrating how notches may be provided in the inner non-magnetic layer in order to support the coil.

Layer 3 surrounds layer 4. Layer 3 provides structural support for the coil whereas layer 4 protects the outer surfaces of the coil. Generally, during assembly, on the outside of layer 3 the notches for the coil are pre machined and the depth of notch is deep enough to bury the coil into the notches. The coil is wrapped over layer 4 and buried into the premade notches and then just slide layer 4 into layer 3. The notch arrangement of layer 3 is shown in FIG. 3.

Polyetheretherketone (PEEK) is a thermoplastic that is non-metallic and has a high resistance to corrosion and good mechanical strength. Other thermoplastics exist that may be used for the purpose of these layers (e.g. layer 3 and/or layer 4) include Teflon, or TORLON.

Layers 3 and 4 and the coil can be supported in many ways within the pipe, one of which is shown in FIG. 1 where two coil supporting members 6 (in this case in the form of a disk positioned at each end) are shown holding layers 3, layer 4 and layer 2 in position and connecting to layer 1.

The coil supporting member 6 is configured to allow fluid flow within the pipe. It will be appreciated that the coil supporting member should minimize disruption to the fluid flow within the pipe. In this case, the coil supporting members each comprise three legs 6*c*, each leg configured to support the coil at one end and to connect to the outer layer at the other end. It will be appreciated that embodiments may have coil supporting members with other numbers of legs. The material for the support structure could be a suitable thermoplastic or even metal if it is positioned a distance of more than 1 coil diameter away axially from the coil itself (e.g. so that the metal does not affect the magnetic field).

As shown in FIG. 1, the 4 layers shown are an example of assembling the coil in cylindrical geometry and providing shielding from the environmental factors. Any other technology that will provide proper geometry of the coil and will incorporate protection of the coil from the environment will also work. For example, epoxy resin may be used to build coil assembly to replace layer 3 and layer 4. The coil may be pre machined with solid copper wire (thicker than AWG 14) so it can hold the shape after it is machined. A coil may be encased by a suitable proper epoxy resin (e.g. using resin curing or cross-linking technology).

The magnet lining layer 8 is used to isolate heat transfer between Pipe 1 and the permanent magnet 9. The material of lining layer 8 could be for example aerogel or a similar material having a good heat insulation quality between pipe layer 1 and the permanent magnet 9.

Figure 4:
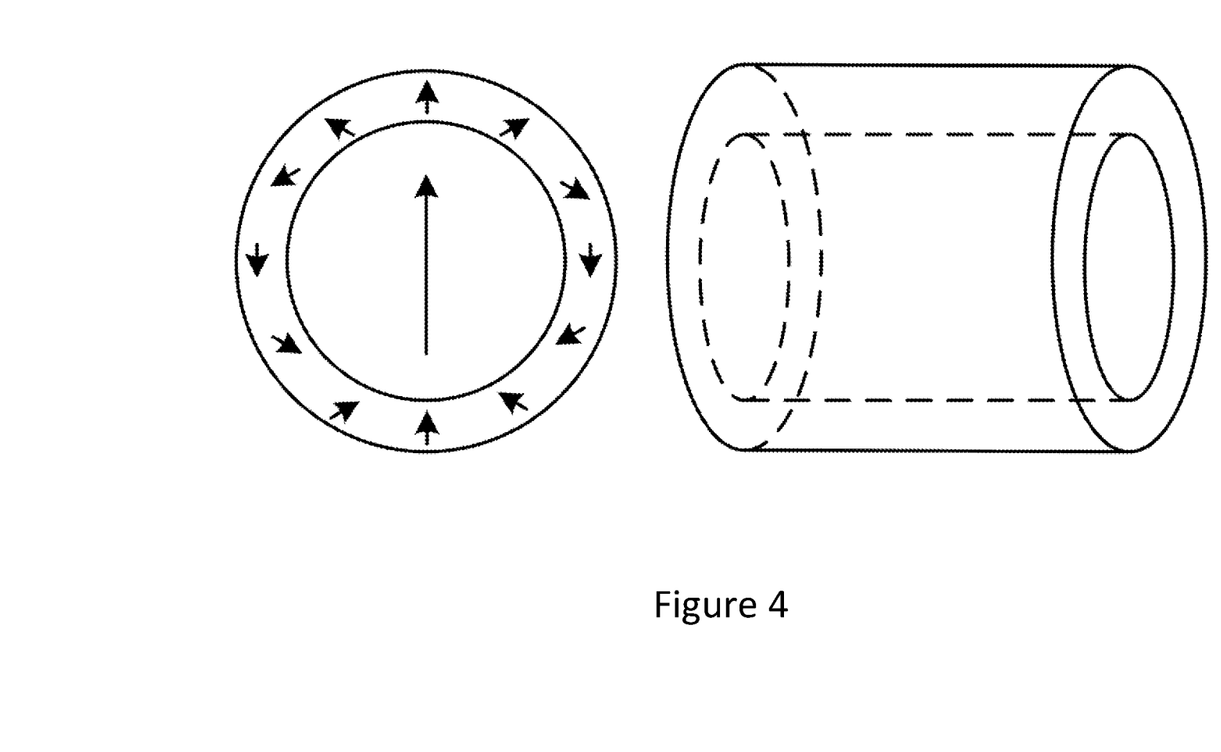
FIG. 4 is a schematic cross-sectional diagram and outline drawing of a Halbach magnet where the arrows in the cross-sectional diagram denote the directions of the permanent magnetic field created by magnet blocks.

The permanent magnet assembly 9 (typically a Halbach magnet assembly) will create a strong homogenous permanent magnetic field (200 to 2000 Gauss) for the sweet spot area. The length of permanent magnet assembly 9 will be close to the coil length. Other magnet systems such as a 2-pole U-shape permanent magnet assembly, or a Helmholtz coil can be used instead of a Halbach magnet.

Assembly/Method of Manufacture

Assembly Description

Assembly of the pipe system 10 will generally follow the procedure below utilizing the following parts list.

1) Parts List
   a. Layer 1 pipe with internal and external threads for both ends to connect with coil supporting disk 6 and flange 7.
   b. Layer 2 pipe to optimize the Q factor of Coil 5 and shield coil 5 from external RF noise.
   c. Layer 3 to protect the coil 5.
   d. Layer 4 with notches on its outside to form the coil frame.
   e. Copper wire to form the coil 5.

f. 2 pieces of coil supporting disk 6 to fix the coil assembly and Layer 2 pipe inside Layer 1 pipe.

g. 2 pieces of off-shelf standard flange 7 to connect with other pipe system.

h. Magnet lining layer 8.

i. Assembly of permanent magnet 9.

2) Assembly Procedure

1) Bury copper wire 5 into the premade notches outside of Layer 4.

2) Slide Layer 4 with Coil 5 into Layer 3 to form the Coil Assembly.

3) Screw coil supporting disk 6 into Layer 1 pipe and put the assembly in vertical position.

4) Slide Layer 2 pipe into Layer 1 pipe and push it against coil supporting disk 6, the front edge of Layer 2 should be sandwiched between Layer 1 and outside bump out ring on coil supporting disk 6.

5) Drop the Coil Assembly into Layer 2 pipe and locate its position to make sure Layer 4 of the Coil Assembly is sitting against the top of inside bump out ring on coil support disk 6.

6) Make sure all layers (1, 2, 3, 4) are in a vertical position and Layer 2, 3 and 4 are connected with coil supporting disk 6 properly.

7) Screw the second piece of coil supporting disk 6 into top end of Layer 1 until the top end of Layer 2, 3 and 4 are connected with the second piece coil supporting disk 6 properly.

8) Install the permanent magnet 9 (with attached lining layer 8) around Pipe 1

9) Connect Flange 7 with Pipe 1 for both ends.

It will be appreciated that other embodiments may be manufactured in other ways. For example, in another embodiment the coil may be machined such that the coils is configured to hold the shape after it is machined; and then encasing the coil in an epoxy resin to form at least part of the inner non-magnetic layer.

Although the present invention has been described and illustrated with respect to preferred embodiments and preferred uses thereof, it is not to be so limited since modifications and changes can be made therein which are within the full, intended scope of the invention as understood by those skilled in the art.

REFERENCES

1. J. D. Jackson, Classical Electrodynamics, $3^{rd\ ed.}$, 1998, Wiley

The invention claimed is:

1. A pipe system for enabling nuclear magnetic resonance (NMR) analysis of gases and liquids within the pipe system comprising:

at least one inner non-magnetic layer having an inner diameter D1 defining an inner fluid passage and an outer diameter D3, the at least one inner non-magnetic layer operatively supporting an NMR coil having an outer diameter D2;

an outer non-magnetic layer and where the at least one inner non-magnetic layer is operatively supported within the outer non-magnetic layer to define an outer fluid passage between the at least one inner non-magnetic layer and the outer non-magnetic layer, the outer fluid passage having an outer diameter D4.

2. The pipe system as in claim 1, where D4/D2=$\sqrt{2}$ with a better matching accuracy than 2%.

3. The pipe system as in claim 1, wherein the outer non-magnetic layer is titanium alloy, hastelloy alloy or inconel alloy.

4. The pipe system as in claim 1, wherein the pipe system comprises an outer shield layer that is operatively connected to the inside of the outer non-magnetic layer and is configured to constrain the magnetic field generated by the coil within the inner shield layer.

5. The pipe system as in claim 4, wherein the outer shield layer comprises a non-magnetic layer.

6. The pipe system as in claim 4, where the outer shield layer is copper or a material having a higher conductivity than copper.

7. The pipe system as in claim 4, wherein the outer shield layer length is at least four times D2.

8. The pipe system as in claim 1, where the coil is copper or a material having a higher conductivity than copper.

9. The pipe system as in claim 1, wherein the at least one inner non-magnetic layer is two thermoplastic layers and the coil is supported by a first inner thermoplastic layer and a second thermoplastic layer surrounds the first inner thermoplastic layer.

10. The pipe system as in claim 1, wherein the inner non-magnetic layer comprises one or more of: a thermoplastic, polyetheretherketone (PEEK), Teflon and TORLON.

11. The pipe system as in claim 1, wherein the outer layer material is a non-magnetic metallic material, or a nonmetallic material.

12. The pipe system as in claim 1, wherein the outer layer material comprises one or more of: titanium, titanium alloy, hastelloy alloy, inconel alloy, beryllium copper alloy, and fiberglass reinforced plastic.

13. The pipe system as in claim 1, wherein the Q-factor, or quality factor, of the resonant circuitry is between 5 and 10.

14. The pipe system as in claim 1, wherein the Q-factor, or quality factor, of the resonant circuitry is above 20.

15. The pipe system as in claim 1, wherein the coil length is at least two times of D2.

16. The pipe system as in claim 1, further comprising at least one coil supporting member, the at least one coil supporting member being configured to support the coil in position with respect to the outer layer and to allow fluid flow within the inner and outer fluid passages.

17. The pipe system as in claim 1, wherein the inner layer comprises: a coil layer configured to provide structural support for the coil; and a protection layer configured to protect the outer surfaces of the coil.

18. The pipe system according to claim 16, wherein the coil layer comprises one or more notches configured to receive the coil.

19. A method of manufacturing a pipe system for enabling nuclear magnetic resonance (NMR) analysis of gas and liquids within the pipe system, the method comprising:

providing at least one inner non-magnetic layer having an inner diameter D1 defining an inner fluid passage and an outer diameter D3, the at least one inner non-magnetic layer operatively supporting an NMR coil having an outer diameter D2;

providing an outer non-magnetic layer and where the at least one inner non-magnetic layer is operatively supported within the outer non-magnetic layer to define an outer fluid passage having a diameter D4 between the at least one inner non-magnetic layer and the outer non-magnetic layer.

20. The method of claim 19, wherein copper coil is produced by winding copper wire around a coil layer, the coil layer forming at least part of the inner non-magnetic layer.

21. The method of claim 19, wherein the method comprises:
  machining the coil such that the coil is configured to hold the shape after it is machined; and
  encasing the coil in an epoxy resin, the epoxy resin forming at least part of the inner non-magnetic layer.

* * * * *